United States Patent
Cucala Escoi et al.

(10) Patent No.: US 7,364,755 B2
(45) Date of Patent: Apr. 29, 2008

(54) MODIFIED CALCIUM PHOSPHATE EXCIPIENT

(75) Inventors: Joan Cucala Escoi, Barcelona (ES); Montserrat Gallego Luengo, Barcelona (ES); Arturo Siles Ortega, Barcelona (ES)

(73) Assignee: Synthon IP Inc., Gainesville, VA (US)

( * ) Notice: Subject to any disclaimer, the term of this patent is extended or adjusted under 35 U.S.C. 154(b) by 401 days.

(21) Appl. No.: 10/882,669

(22) Filed: Jul. 2, 2004

(65) Prior Publication Data

US 2005/0031682 A1    Feb. 10, 2005

Related U.S. Application Data

(60) Provisional application No. 60/484,669, filed on Jul. 7, 2003.

(51) Int. Cl.
*A61K 9/14* (2006.01)

(52) U.S. Cl. .................................. 424/489

(58) Field of Classification Search .................. 424/499
See application file for complete search history.

(56) References Cited

U.S. PATENT DOCUMENTS

| 4,693,750 | A |   | 9/1987  | Bauer et al. |
| 4,744,987 | A |   | 5/1988  | Mehra et al. |
| 5,006,345 | A |   | 4/1991  | Lang |
| 5,169,645 | A |   | 12/1992 | Shukla et al. |
| 5,443,846 | A |   | 8/1995  | Yoshioka et al. |
| 5,585,115 | A |   | 12/1996 | Sherwood et al. |
| 5,700,410 | A |   | 12/1997 | Nakamichi et al. |
| 6,123,964 | A | * | 9/2000  | Asgharnejad et al. ....... 424/489 |
| 6,811,794 | B2 | * | 11/2004 | Burnside et al. ............ 424/468 |

* cited by examiner

*Primary Examiner*—Johann Richter
*Assistant Examiner*—Ali Soroush
(74) *Attorney, Agent, or Firm*—Mark R. Buscher

(57) ABSTRACT

Calcium phosphate modified with a fatty acid wax in a weight ratio of 50:50 to 95:5, respectively, is useful as an excipient.

18 Claims, No Drawings

MODIFIED CALCIUM PHOSPHATE EXCIPIENT

The present application claims the benefit of priority under 35 U.S.C. § 119(e) from U.S. provisional application Ser. No. 60/484,669, filed Jul. 7, 2003, the entire contents of which are incorporated herein by reference.

BACKGROUND OF THE INVENTION

1. Field of the Invention

The present invention relates to a calcium phosphate-based excipient that can be used in making formulations, and to processes of making and using the same.

2. Description of the Prior Art

Solid dosage forms are a convenient way to deliver active agents. Tablets and capsules are common types of solid dosage forms. Generally tablets are made by compressing a solid material, which contains an active substance, in a tablet press. For efficiency and quality reasons in manufacturing, the material is desired to exhibit certain physical characteristics. For example, the material should be free-flowing (to insure that the space of the die cavity in the press is uniformly filled), should not be adhesive to the tablet punch surface (to be readily ejected from the punch faces) and possess sufficient cohesiveness to insure that the solid dosage form remains intact after compression. Since most of the active ingredients, particularly most of the pharmaceutically active ingredients, do not have all of these properties, inactive ingredients, i.e., "excipients," are frequently added to the active ingredient in order to impart desirable characteristics. Additionally, excipients known as fillers or solid diluents are sometimes added to increase the bulk weight of the material to be tabletted to a more practical size for compression/tabletting.

Furthermore, other kinds of excipients may be added to the tabletting material for reasons other than manufacturing, e.g. to allow the tablet to disintegrate after administration, to modify the release of the active agent from the tablet, to stabilize the active agent, to protect the tablet composition against moisture, etc. Some excipients have more than one effect. For instance, microcrystalline cellulose is an excipient that has good binding properties and provides good disintegration properties.

Several general schemes are available for combining the active agent and excipient(s) to form the tablettable material. In one scheme, the active agent is granulated with one or more excipients into free flowing granules, which are then mixed/homogenized with the remaining solid excipients, if any, and the resulting free flowing mixture is then tabletted. There are three general and well known methods for performing the granulation: wet granulation, dry granulation and hot-melt granulation. Granulation is also often used to provide a modulated release of the active from the tablet composition due to both the physical effect of granulation as well the kind of excipients used in modifying release rate.

A simpler and more modem tabletting process however involves the direct compression of a solid mixture of the active agent and excipients into a tablet, without granulating or modifying the active agent. While this direct compression process is the simplest and cheapest, it also has its limitations. For instance, only a limited number of excipients are suitable for this process; i.e., excipients with excellent binding properties, good flow and high compressibility. Direct tabletting excipients should also have a high uptake capacity for the active agent in that active agents are frequently difficult to compress. Further, the excipient should not have too high a density or else segregation of the different parts of the material to be compressed can occur. Optimally, the resulting tablets are generally intended to have low friability and high fracture resistance.

Some of these requirements are contradictory. For example, high tablet fracture resistance is associated with a large area of contact between the active agent and the diluent/binder inside the tablet. This can be achieved by the use of diluent and binder in the form of fine particles. However, fine-particles tend to have poor flow properties which limits their suitability in high speed processes.

Direct compression is also limited in making a modified release dosage form, i.e. a non-immediate release tablet. In general, there are only a limited number of suitable excipients for making controlled release dosage forms by direct compression tabletting. An example of such a suitable excipient is hydroxypropylmethylcellulose (HPMC).

In addition to making tablets, active agents can be formulated into other solid dosage forms such as capsules. A capsule generally contains the active material encapsulated such as by a hard or soft gelatin capsule. The active material is again normally combined with excipients for bulk, handling, etc., reasons. A common process for forming a capsule dosage form involves granulating the active agent with one or more excipients, optionally coating the granulates, and filling the capsule with the granulate. This is especially useful for modified release dosage forms. Indeed, a mixture of granules having different release characteristics, e.g. immediate, moderate and delayed, can be filled into a capsule to provide an overall sustained release profile.

One common excipient is calcium phosphate in one of several forms, e.g., monobasic, dibasic, and tribasic in anhydrous or hydrated form. Calcium phosphate is considered to be suitable for both granulation and direct compression tabletting processes because of its compaction properties, good binding properties and good flow properties of the coarse-grade material. However, calcium phosphate has certain disadvantageous properties. For instance, calcium phosphates are abrasive and at higher pressures the tablet can exhibit lamination and capping. This phenomenon can be observed when the calcium phosphate comprises a substantial proportion of the formulation and is exacerbated by the use of deep concave tooling. Further, calcium phosphate can be incompatible with some active agents, such as pH-sensitive pharmaceutical active agents. The surface of milled anhydrous dibasic calcium phosphate is alkaline and consequently it is generally not used with active agents that are sensitive to alkaline pH. On the other hand, the coarse grade form has an acidic surface environment. Beyond this, the overall pH of the calcium phosphate can vary by brand from acidic to alkaline. The pH can have important implications for stability of the dosage form.

Another limitation of calcium phosphate is its inability to provide a controlled/modified release rate. Generally an additional excipient having release modulation properties must be incorporated into the dosage form, such as in the tablet matrix or as a coating thereon.

Another excipient is a wax. Waxes are hydrophobic compounds, many of which are known for use in oral solid dosage pharmaceutical formulations as lubricants or as a sustained-release matrix (for example, see EP 665010). In general, the release rate decreases with increasing wax content, but at the same time compression properties are worsened with increasing wax content. Waxes generally have poor flow properties, which makes them less suitable or, particularly at higher contents necessary to produce controlled-release profiles, unsuitable for direct compression. Instead, these hydrophobic substances usually have to be pre-treated with the active agent when used to make a controlled release dosage form. Some of the more common fatty acid waxes have typically been used as follows:

Glyceryl Behenate is used as tablet and capsule lubricant: 0.5-5%, and as matrix for sustained release: 10-30%.

Glyceryl Palmitostearate is used as tablet and capsule lubricant: 0.5-5%, and as matrix for sustained release: 10-50%.

Hydrogenated Castor Oil is used as tablet and capsule lubricant: 0.1-2%, and as matrix for sustained release: 5-10%.

Glyceryl behenate and glyceryl palmitostearate are each available in grades that can be used for direct compression (e.g. COMPRITOL ATO 888 from Gattefossé and PRECIROL ATO 5 from Gattefossé, respectively), but usually the compositions including them are prepared by pre-granulation of the wax with the active agent and other excipients before compression because of poor flowing properties of the wax itself Attempts have been made over the years to improve or modify excipients so that their unsuitable properties are substantially eliminated while retaining the beneficial characteristics. Some of these approaches involve combining two or more excipients into a singular multicomponent excipient wherein the several starting excipients are put into intimate contact generally via a specific process. Such multicomponent excipients are generally not a mere mixture as would be formed by plain mixing of the solid components together. Rather, usually the resulting excipient exhibits some degree of mutual agglomeration, impregnation, or coating of the excipients. In particular, celluloses have been studied in this regard.

For example, DE-C 3 506 276 discloses a combination of lactose monohydrate and powdered cellulose for direct tabletting. This composition is purported to have a high binding capacity.

DE-A 35 05 433 (U.S. Pat. No. 5,006,345) discloses an intimate mixture of lactose monohydrate, polyvinyl pyrrolidone and crosslinked, insoluble polyvinyl pyrrolidone. The mixture is generally formed by granulating the three components. The excipient is purported to have excellent flow properties and can provide, without further addition of a disintegrant, a rapidly disintegrating tablet.

U.S. Pat. No. 4,744,987 discloses a particulate co-processed microcrystalline cellulose and calcium carbonate composition wherein the respective components are present in a weight ratio of 75:25 to 35:65. The excipient has comparable tabletting properties as the cellulose itself, but at a lower cost.

U.S. Pat. No. 5,169,645 discloses directly compressible granules made by admixing flow improving additives into melted wax followed by cooling and granulation. The wax-containing granules are purported to have improved flow properties. The additives disclosed include, inter alia, a variety of polymers as well as finely divided silica, particulate sugars, and calcium gluconate, calcium phosphate, and calcium carbonate particles.

U.S. Pat. No. 5,585,115 discloses a pharmaceutical excipient based on a co-processed microcrystalline cellulose and from about 0.1% to about 20% silicon dioxide particles, wherein the microcrystalline cellulose and silicon dioxide are in intimate association with each other. The intimate association is generally formed by spray drying an aqueous slurry of the two excipients. Such an excipient improves the compressibility of the cellulose.

Thus, in general there is a need for an excipient with good compressibility and binding properties. In particular, there is a need to improve the properties of calcium phosphate especially for use in solid dosage forms, including improving the abrasiveness, compatibility with pH-sensitive active agents, and/or release rate modifying effect.

SUMMARY OF THE INVENTION

The present invention is based on the discovery that calcium phosphate can be modified with a fatty acid wax and further that such a modified calcium phosphate can provide advantageous properties. Accordingly, a first aspect of the invention relates to an excipient composition comprising calcium phosphate modified with a fatty acid wax, wherein a weight ratio of calcium phosphate to wax is within the range of 50:50 to 95:5, respectively. The excipient composition is generally provided in a free flowing particulate form and the fatty acid wax is generally selected from palmitic acid, behenic acid, stearic acid, glyceryl behenate, glyceryl palmitostearate, hydrogenated castor oil, and mixtures thereof. The particles generally have an average size in the range of 20 to 1000 microns, typically 50 to 500 microns, and in some embodiments from 125 to 250 microns. The calcium phosphate is normally an anhydrous dibasic calcium phosphate.

Another aspect of the invention relates to a solid dosage form comprising an effective amount of an active agent and the above described excipient composition. The dosage form may optionally contain one or more auxiliary excipients. The solid dosage form includes tablets and capsules and can be an immediate release or a non-immediate release composition. The active agent is preferably a pharmaceutically active agent and the solid dosage form is preferably adapted for oral administration.

A further aspect of the invention relates to a process for making a tablet, which comprises: dry mixing the above-described excipient composition with an active agent and optionally one or more other excipients to form a tablet blend; and compressing at least a portion of the tablet blend into a tablet. The process can be used to form non-immediate release tablets owing to the modified calcium phosphate excipient of the present invention being used therein. The tablets produced, regardless of the release profile, can be further coated such as with an enteric coating, etc.

An additional aspect of the invention relates to a process, which comprises: granulating the above-described excipient composition with an active agent to form an active granulate; and compressing at least a portion of the active granulate, optionally with additional excipients, into a tablet. The granulating step can comprise any of the known granulating processes including wet granulating the active agent with the excipient composition.

Another aspect of the present invention relates to a process, which comprises coating calcium phosphate particles with a fatty acid wax to form a modified calcium phosphate in particulate form having a weight ratio of calcium phosphate to wax within the range of 50:50 to 95:5, respectively. The "coating" step, which is used in a broad sense as described hereinafter, is generally carried out by melt granulating the calcium phosphate and wax. The process can be used to form any of the modified calcium phosphate excipients of the present invention.

Still another aspect of the invention relates to a particle, consisting essentially of a calcium phosphate particle having a fatty acid wax at least partially coated thereon, impregnated therein, or both; said particle have a size within the range of 125 to 250 microns and said calcium phosphate and wax being present in a weight ratio of 50:50 to 95:5.

An additional aspect of the present invention relates to a process for improving the properties of calcium phosphate, especially pharmaceutical grade calcium phosphate, which comprises melt granulating calcium phosphate particles with a fatty acid wax in a weight ratio of 50:50 to 95:5, of calcium phosphate:fatty acid wax, to form granules.

DETAILED DESCRIPTION OF THE INVENTION

The present invention relates to a modified calcium phosphate excipient and its uses. It has been discovered that calcium phosphate can be modified with wax to provide a useful excipient, especially in direct compression tabletting. The calcium phosphate is "modified" in that the fatty acid wax becomes intimately associated with the calcium phosphate particle. Such an intimate association is not a mere admixture of the two ingredients. However, it is not believed to involve a chemical interaction. Instead the wax has been in some manner integrated with or adsorbed on/in the calcium phosphate particles, e.g., the calcium phosphate particle is at least partly, coated, impregnated, or otherwise agglomerated with the wax. Magnifications of the resultant particles indicate that the wax is tied, at least partly to the particles of the calcium phosphate. It is this new singe particle having wax and calcium phosphate that is termed "modified" calcium phosphate. Surprisingly, the modified calcium phosphate of the present invention can provide improved properties. For example, the abrasion and capping issues normally associated with calcium phosphate can be reduced or avoided by modifying with fatty acid wax without simultaneously obtaining the poor flow characteristics associated with fatty acid wax. Additionally, the modified calcium phosphate of the present invention can provide a modified release profile, even when tabletted by simple direct compression with or without other, conventional release modifying agents. It is believed that such an effect is caused by the modified calcium phosphate forming a modified release matrix formed in part of the wax. In short, the modified calcium phosphate of the present invention can be provided as an excipient with all the advantages of calcium phosphate and of wax but essentially without their respective disadvantages.

The calcium phosphate to be modified and/or used in the present invention includes any type of solid, particulate calcium phosphate such as the monobasic, dibasic and tribasic types in both anhydrate and hydrate configurations. A variety of types are commercially readily available. In general, calcium phosphates are usually manufactured by reacting very pure phosphoric acid with calcium hydroxide, $Ca(OH)_2$, obtained from limestone, in stoichiometric ratio in aqueous suspension followed by drying at a temperature which will allow the correct hydration state to be achieved. After drying, the coarse-grade material (e.g. greater than 50 microns) is obtained by means of a classification unit; the fine particle-size material (e.g. less than 20 microns) is obtained by milling. However, the calcium phosphate used in the present invention is not limited to calcium phosphates made by this general method. The calcium phosphate is preferably dibasic calcium phosphate (calcium hydrogenphosphate), in an anhydrate or dihydrate form.

Dibasic calcium phosphate dihydrate is a nonhygroscopic, relatively stable material at room temperature. However, under certain conditions of temperature and humidity, it can lose water of crystallization below 100° C. This has implications for certain types of packaging and aqueous processes since the loss of water of crystallization appears to be initiated by high humidity and by implication high moisture concentration in the vicinity of the particles.

Dibasic calcium phosphate anhydrous is a nonhygroscopic, relatively stable material. Under conditions of high humidity it does not hydrate to form the dihydrate.

Dibasic calcium phosphate is known to be useful as a diluent/binder in wet granulation and in direct compression. Grades of dibasic calcium phosphate available for direct compression include dihydrate forms; e.g. DI-TAB from Rhodia (pH 7.4, avg. particle size 180 microns); DICAFOS from Budenheim; EMCOMPRESS from Penwest and anhydrous forms; e.g. A-TAB from Rhodia (pH 5.1, avg. particle size 180 microns); DICAFOS A/AN from Budenheim; ANHYDROUS EMCOMPRESS from Penwest (avg. particle size 136 microns). Any of these forms of dibasic calcium phosphate are suitable for use in making the modified calcium phosphate of the present invention.

The calcium phosphate is not particularly limited in particle size. Generally the particles have an average particle size in the range of 5 microns to 500 microns. The particles are preferably "coarse grade" meaning an average particle size of at least 50 microns and generally within the range of 75 to 250 microns such 100 to 200 microns. While coarse grade calcium phosphate is preferred, it has been found that even milled calcium phosphate, which otherwise is less suitable or even unsuitable for direct compression, can be now, when modified according to the invention, be used in direct compression tabletting techniques. Such finer grades of calcium phosphate typically have an average particle size of 5 to 50 microns, more typically 5 to 20 microns such as 9 to 15 microns.

The "fatty acid wax" with which the calcium phosphate is modified is a material, being solid at room temperature (i.e. 25° C.), that is made of one or more fatty acids and/or esters of a fatty acid(s) with a mono- and/or polyfunctional alcohol, wherein the preferred alcohol is glycerol. Generally the fatty acids have 12 to 25 carbon atoms, more typically 15 to 20 carbon atoms and the esters generally contain 13 to 80 carbon atoms more typically 18 to 60 carbon atoms. Examples of the fatty acid waxes are palmitic, behenic, or stearic acid, glyceryl behenate, glyceryl palmitostearate, hydrogenated castor oil, and other natural waxes including microcrystalline waxes. Mixtures of various kinds of fatty acids and fatty acid esters as well as mixtures of waxes all fall under the meaning of "fatty acid wax" in the invention. The fatty acid wax normally has a melting point or range that begins within the range of 40° C. to 140° C., more typically 50° C. to 100° C., however such is not required.

Usually the fatty acid wax is glyceryl behenate or glyceryl palmitostearate. Glyceryl behenate is the ester of behenic acid and glycerol with a melting point of about 70° C. It appears as a fine white powder with a faint odor. Glyceryl palmitostearate is the ester of palmitic/stearic acids and glycerol with a melting point of about 55° C. It appears as a fine white to off-white powder with a faint odor. Commercially available glyceryl behenate and glyceryl palmitostearate are available as COMPRITOL ATO 888 from Gattefossé and PRECIROL ATO 5 from Gattefossé, respectively.

The amount of wax in the modified calcium phosphate is not particularly limited and is generally within a calcium phosphate:fatty acid wax weight ratio of 50:50 to 95:5, more typically 60:40 to 85:15, and in some embodiments 70:30 to 80:20 such as about 75:25. These weight ratios apply to individual particles as well as to a particle population. In the latter case it is understood that not every particle is required to fall within the weight ratio range, so long as the overall content or average satisfies the weight ratio range. In general using more wax tends to increase the likelihood of flow difficulties for the resulting particulates due to size, the increased formation of pure wax particles and/or interparticle adhesion, etc. Using less wax can minimize the effect of the modification. The above ranges seek to compromise these and other trade-offs.

The average particle size of the modified calcium phosphate can be any suitable size for an excipient and typically is within the range from about 20 microns to about 1000 microns, typically about 50-500 microns, and in some embodiments about 125 to 250 microns. The particles that make up the particulate form can have various shapes. For process considerations, the particles are preferably granules, e.g. a modified calcium phosphate made by a granulation process, and can be substantially spherical or angular. Preferably the particulate is monodisperse such that at least 50%, preferably at least 66%, of the particles have a particle size within 20 microns of the average particle size. The particle size is a function of the starting particle size of the calcium phosphate, the amount of wax used in the modification and the method of modifying, as is discussed more thoroughly herein after. Frequently the particle size is essentially proportional to the relative amount of the fatty acid wax used, but such is not required. Indeed, if the calcium phosphate is coarse grade with high porosity, the wax may tend to fill in the pores and thus not linearly increase the particle size or layer thickness, if any.

The wax modified calcium phosphate may also comprise auxiliary excipients such as colorants, surfactants, release rate modifying agents, lubricants, release agents, and antioxidants. When auxiliary excipients are present in the modified calcium phosphate particles, such auxiliary excipients are preferably present in minor amounts, typically less than 10% by weight. Generally the excipient composition does not contain the auxiliary excipients of a release rate modifying agent or a lubricant because these functions can be achieved without the need for auxiliary excipients. Indeed, usually the modified calcium phosphate particles do not contain any auxiliary excipient; i.e. the particles consists of calcium phosphate and fatty acid wax.

The modified calcium phosphate excipient of the present invention is generally directly compressible into tablets. In preferred embodiments of the present invention, the excipient has similar compressibility as compared to standard commercially available coarse grades of calcium phosphate and is substantially more compressible than milled grades of calcium phosphate. Likewise, the excipient of the invention is normally free-flowing, before being incorporated into a dosage form at least, and suitable for use in tabletting processes and machinery. The angle of repose and/or a flow rate (the time to flow through an aperture of pre-determined size, e.g. as described in Ph.Eur.) are suitable measurements used to determine the flow characteristics of a particulate. The measurement is subject to the experiment conditions and experimenter, but measurements in a comparative test show that the excipient of the invention is superior to the wax itself, better than a plain physical mixture of both components and usually comparable with the (unmodified) calcium phosphate starting particulate. In general terms, the modified calcium phosphate and/or excipient composition containing the same has an angle of repose that is not greater than 45°, normally within the range of 20° to 40°.

The wax modification of the calcium phosphate can also reduce the original surface area and surface pH of the calcium phosphate. In consequence, interaction of the active agent with the surface of calcium phosphate (which otherwise may exhibit undesired acidic or alkaline pH or may catalyze decomposition reactions such as oxidations) is minimized and thus the stability of pH sensitive actives is enhanced. Further, the stickiness of the active agent to the tablet punch can also be reduced by the fatty acid wax modified calcium phosphate excipient of the present invention. The modified calcium phosphate can also provide reduced abrasiveness and lower density than the original calcium phosphate, which can lead to a decrease in the need of a lubricant and the danger of segregation within the tabletting procedure, respectively. On the other hand, many of the advantageous properties of the calcium phosphate are retained.

Moreover, the modified calcium phosphate and/or excipient composition containing the same can provide surprising advantages in oral dosage forms. For example, even though the excipient contains a phosphate that is inherently soluble in acidic media, the excipient can provide gastric resistance through the stomach and even maintain some integrity during the gastrointestinal transit. Additionally, active agents that are sensitive to pH could be protected against decomposition in the stomach by being formulated with the modified calcium phosphate excipient of the present invention.

Those skilled in the art will appreciate that the names and grades of calcium phosphate and fatty acid waxes utilized in the present invention are not determinative of the usefulness of the novel excipient. Rather, as previously mentioned, it has been surprisingly discovered that a calcium phosphate particle may be modified with a fatty acid wax to obtain a solid, free flowing material having technological properties and use potential that are superior to the properties of the respective compounds when used alone or in a simple combination.

A preferred embodiment of the modified calcium phosphate/wax excipient of the present invention is a granulated solid product of substantially white color, insoluble in water, approximately regular in shape, and relatively uniform in size. It is a hydrophobic surface showing no hygroscopicity. It has excellent flowability and it maintains good compressibility; i.e. comparable to calcium phosphate itself. It has a lower density than calcium phosphate itself, thus reducing the chance for segregation problems in drum hoppers during tabletting. It exhibits higher bulk or tap density and surprisingly less true density than a simple mixture of the same composition, which indicates a reduction in pore sizes and surface area.

The fatty acid wax modified calcium phosphate of the present invention can be made by a process that generally comprises coating the calcium phosphate particles with a sufficient amount of wax to provide a ratio of 50:50 to 95:5 (calcium phosphate:wax). "Coating" is used in its broadest sense of placing the wax on, in, or over the calcium phosphate particles in partial or complete coverage of the particle and specifically includes partial or complete surface coating, void filling, adsorption on and/or impregnating of the calcium phosphate particle. The coating step can also be characterized as co-processing. The coating is performed in the absence of an active agent in order to form a modified calcium phosphate excipient. The coating operation, which may comprise one or more steps, results in a particulate composition. Preferably the coating step comprises applying the fatty acid wax in a flowable state to the calcium phosphate. A "flowable state" means that the wax has liquid or liquid-like properties and is generally achieved by heating the wax to at least its softening point, normally about its melting point or higher, or by dissolving or suspending the wax in a solvent to form a solution or slurry, respectively. By applying the wax in a flowable state, coating of the calcium phosphate particles can be carried out by granulation methods including hot melt granulation, melt extrusion, and wet granulation, as well as by spraying and spray-drying methods. Melt granulation is a preferred technique.

Melt granulation generally comprises three phases: softening/melting phase, agglomerating/granulating phase, and a cooling phase. The phases can be distinct or overlapping. Suitable processes for making the excipient of the present invention are described below.

Powdered or granulated calcium phosphate is mixed with the solid fatty acid wax in desired amounts, e.g., in a weight ratio between 50:50 to 95:5, in suitable mixer equipment. The mixture is heated to a temperature necessary to soften or melt the fatty acid wax in suitable heating equipment such as a high shear granulator or extruder. The temperature depends on the nature and melting point of the fatty acid wax, the relative amount of the wax and the equipment used. Conventional pharmaceutically useful waxes exhibit a melting point from about 40° C. to about 100° C. For instance, glyceryl behenate has a melting point of about 70° C. and suitable temperatures for the mixture are from 50° C. to 80° C. In general, the recommended temperature of granulating is from 5° C. below the melting point of the wax up to 5° C., more typically 2° C., above the melting point of the wax. In a shear mixer/granulator apparatus, heating to the wax mixture above the melting point to form a true liquefied wax can be disadvantageous in that the flowability of the resulting granulate is usually reduced. For example, glyceryl behenate, which has a melting range of 68-72° C., is satisfactorily "melted" by targeting 71° C. Reaching a wax temperature a few degrees higher or lower than 71° C. generally does not adversely affect the resulting granulates. The heating can be performed by a heated jacket, for example, but preferably involves microwave energy. Without wishing to be bound by theory, it is believed that microwave energy heating provides more even heating and heat transfer than simply using external heating such as from a heated jacket and thus avoids or reduces any temperature differential between the sides of the vessel and the center of the vessel. The microwave energy can be the sole heating source or used in combination with other heating sources. Once the wax has been softened and/or melted and sufficiently homogenized with the calcium phosphate particles, an intimate mixture of wax on/within calcium phosphate is provided.

The intimate mixture of calcium phosphate with the wax is then granulated while hot, that is plastic. Conventionally, it is achieved by high speed/sheer mixing the plastic material, using an impeller and a chopper in a granulator, or by extruding the hot mass in an extruder. Advantageously, the step of melting and granulating are performed in the same equipment and it should be noted that all of these operations are advantageously performed in an inert atmosphere such as under vacuum or nitrogen.

The conditions of stirring/chopping depend on the equipment used but they are conventional to a skilled person. The moment of granulate formation may be indicated e.g. by a maximum of torque resistance, e.g. of the impeller in the mixer or the screw in the extruder. No surface active agent is usually necessary to produce granules. Under certain circumstances, even a practically spherical product, e.g. pellets of regular size up to 2-3 mm, can be produced by this technique.

The formed granules are then cooled, preferably with gentle mixing, so that also the wax solidifies, and a solid granulated product is the produced. The solidified product is removed from the equipment once the temperature drops to essentially ambient. No specific cooling regimen is prescribed, however it is practical that the first phase of cooling (up to complete solidification of the granules) is forced (by a cooling medium), while the second phase may be spontaneous. The cooling phase can be performed in the same vessel as the heating and/or granulating phases or it can be performed in a separate vessel or mixer. Correspondingly, the granulation process can be carried out as a batch process, a semi-batch process or a continuous process. Optionally, the solid granules are screened/sieved to obtain a granulated material of desired particle size.

No solvent is usually required for the melt granulation coating process as the flowable state wax is sufficiently distributable to form granules of wax modified calcium phosphate. However, a solvent can be used if desired. Typically a solvent is only used in a wet granulation process. Here the solvent is one in which the wax is soluble such as a hydrocarbon or a halogenated hydrocarbon, e.g., chloroform or dichloromethane. The solution may be heated to assist the solubility/homogeneous dispersion of the wax, but such is not strictly necessary. The wax solution is combined with the calcium phosphate particles by any suitable method, e.g. adding the wax solution to the calcium phosphate, adding the solvent to a blend of the wax and calcium phosphate for in situ solution formation, etc., and then mixed to form a granulate as described above. The solvent is removed by drying after the solid granules are obtained or even within the process of granulation. Any conventional method of drying may be used. As with melt granulation, any of the granulation processes may be arranged as a batch process, a continual process or as a semicontinual process by using one or more apparatus.

Aside from the granulation techniques, spraying techniques can be used. For example, a solution or slurry of the fatty acid wax in a solvent can be sprayed onto the calcium phosphate and then dried to form a modified calcium phosphate particulate composition. Similarly, a melted or liquefied fatty acid wax can be sprayed onto the calcium phosphate particles followed by cooling to form a modified calcium phosphate particulate composition. In either case, the calcium phosphate particles are preferably in a gas-operated fluidized bed to facilitate uniform coating of the wax and to encourage a particulate product being formed. In general spraying techniques are less economical when the amount of wax exceeds 15% and can be difficult to operate at wax contents of greater than 25%. Suitable spraying conditions, comparable to known processes wherein an active agent is the coating target such as taught in U.S. Pat. No. 6,194,005 can be used in for spraying the calcium phosphate with fatty acid wax to form/maintain a particulate form.

After the wax modified calcium phosphate particulates are formed, the particles may be sorted or mechanically altered according to ranges of particle size depending upon end uses. Furthermore, the particles of the excipient may be reprocessed by the above "melt granulation", optionally with next amount of calcium phosphate or wax, for instance to provide a product of different ratios of components and/or of different particle size, or with an auxiliary excipient such as a dye/colorant. Multiple particulate populations, or portions thereof, can be blended to form an excipient composition, if desired. The modified calcium phosphate particulates can be used per se as an excipient, or additional excipients can be added thereto by conventional blending techniques. For clarity, the excipient composition of the present invention does not include an active agent.

The modified calcium phosphate excipient composition is useful in making a variety of solid dosage forms. A solid dosage form includes tablets, capsules, and sachets, etc. as are well known in the art. The solid dosage form of the present invention comprises an effective amount of an active agent and a fatty acid wax modified calcium phosphate excipient composition.

An active agent is any beneficial or therapeutic compound or compounds such as systemically active therapeutic agents, locally active therapeutic agents, disinfecting agents, chemical impregnants, cleansing agents, deodorants, fragrances, dyes, animal repellents, insect repellents, fertilizing agents, pesticides, herbicides, fungicides, plant growth stimulants, and the like.

The therapeutic agents comprise human and veterinary pharmaceutical active agents including nutraceuticals, vitamins, antioxidants, etc. A wide variety of therapeutically active agents can be used in conjunction with the present invention. The therapeutically active agents (e.g. pharmaceutical agents) which may be used in the compositions of the present invention include both water soluble and water insoluble drugs. Examples of such therapeutically active agents include antihistamines, analgesics, non-steroidal anti-inflammatory agents, anti-epileptics, vasodilators, anti-tussive agents and expectorants, anti-asthmatics, antacids, anti-spasmodics, antidiabetics, diuretics, anti-hypotensives, antihypertensives, bronchodilators, steroids, antibiotics, antihemorrhoidals, hypnotics, psychotropics, antidiarrheals, mucolytics, sedatives, decongestants, laxatives, vitamins, stimulants (including appetite suppressants such as phenylpropanolamine), antifungal agents, and antiviral agents. The above list is not meant to be exclusive.

The locally active agent(s) include breath fresheners, local anesthetics, oral antiseptics, anti-inflammatory agents, hormonal agents, antiplaque agents, acidity reducing agents, and tooth desensitizers. This list is not meant to be exclusive.

A non-exhaustive list of pharmaceutically active agents useful for making solid dosage forms with the excipient of the invention include ibuprofen, acetaminophen, piroxicam (anti-inflammatory); leflunomide celecoxib, rifecoxib (anti-rheumatics); ondansetron, granisetron (antiemetics); paracetamol (analgetics); carbamazepin, lamotrigine (antiepileptic); clozapine, olanzapine, risperidone, citalopram, paroxetine, sertraline, fluoxetine, fluvoxamine, venlafaxine, (antipsychotics/antidepressants); zopiclon, zolpidem (hypnotics); cimetidine, ranitidine, omeprazole (antiulcerics); metoclopramide, cisapride, domperidon (prokinetic); zafirlukast, montelukast (antiasthmatics); pramipexole, selegiline (anti-parkinsonics); zolpidem, zopiclon (hypnotics); doxazosin, terazosin, atenolol, bisoprolol, amlodipine, nifedipine, diltiazem, enalapril, captopril, ramipril, losartan (cardiovasculars); glyceroltrinitrate (vasodilantant); alfuzosin, finasteride (urologic); pravastatin, atorvastatin, simvastatin, gemfibrozil, niacin (hypolipidemics); metformin, pioglitazone, rosiglitazone (antidiabetic); terfenadine, loratadine, fexofenadine (antihistaminic); rivastigmine, donepezil, oxybutynin, olanzapine, sildenafil, bicalutamide, etc. The pharmaceutically active agent, including each of the exemplified drugs listed above, can be used in the free acid/free base form, salt form, anhydrate form, and/or solvated form including hydrates. Preferred pharmaceutically active agents are bisoprolol, venlafaxine, paroxetine, tamsulosin, simvastatin, amlodipine, pramipexole, oxybutynin, zolpidem and their salts. A preferred example of a water insoluble drug is venlafaxine base. A preferred example of a water soluble drug is paroxetine mesylate.

The modified calcium phosphate particulate composition can be used as an excipient composition or material by itself or in combination with other excipients. Some embodiments of an excipient composition include an excipient composition that consists of the wax modified calcium phosphate particles and optionally further containing unmodified calcium phosphate particles and/or particulates of the fatty acid wax. It is preferred that the excipient composition does not contain more than 1% by weight of wax particles, more preferably not more than 0.5%, still more preferably not more than 0.1%. While the amount of unmodified calcium phosphate is not particularly limited, higher amounts tend to dilute the effect of the modified calcium phosphate. Thus, normally the excipient composition does not contain more than 50% by weight, typically not more than 20%, and most typically not more than 5% such as 0 to 1%, of unmodified calcium phosphate. The unmodified calcium phosphate or wax particles can be provided in situ during manufacture of the modified calcium phosphate or deliberately added afterward.

In addition to the modified calcium phosphate, the excipient composition and/or dosage form may contain additional excipients including binders, diluents, and/or auxiliary excipients as described above. For example, if desired, any generally accepted soluble or insoluble inert pharmaceutical filler (diluent) material can be included in the final product. Preferably, the inert pharmaceutical filler comprises a monosaccharide, a disaccharide, a polyhydric alcohol, inorganic phosphates, sulfates or carbonates, and/or mixtures thereof. Examples of suitable inert pharmaceutical fillers include sucrose, dextrose, lactose, xylitol, fructose, sorbitol, calcium phosphate, calcium sulfate, calcium carbonate, microcrystalline cellulose, mixtures thereof, and the like.

The amount of the modified calcium phosphate excipient of the present invention is normally at least 10% by weight, typically at least 20%, more typically at least 30%, and in some embodiments comprises at least 40%, 50%, 60%, or at least 70% of the total weight of the solid dosage form. Generally the amount of the modified calcium phosphate excipient is within the range of 10% to 90%, more typically 20% to 80% of the solid dosage form based on weight. In some embodiments the modified calcium phosphate excipient composition and the active agent, especially a therapeutic or pharmaceutical active agent, taken together total at least 85% by weight of the total dosage form.

The solid dosage forms containing a pharmaceutically active agent are usually adapted for oral administration, although other routes are possible. Such forms can be of the immediate release type or non-immediate release type. "Immediate release" means that at least 80% of the active agent is released from the dosage form within thirty minutes as measured in an in vitro dissolution testing apparatus using 0.1N HCl as the testing media. In practice, the goal of an immediate release dosage form is to deliver all the active agent rapidly upon ingestion. "Non-immediate release" for purposes of the present invention means that 80% of the active is not released until after thirty minutes in the in vitro dissolution testing apparatus using 0.1N HCl. The non-immediate release dosage forms include such conventional release rate terms as modified release, sustained release, delayed release, and extended release.

In order to achieve non-immediate release rates, it is conventional to add a release rate modifying agent to the dosage form as part of the solid matrix or as a coating.

However, it is preferred that the quality and amount of the fatty acid wax modified calcium phosphate excipient of the present invention reduces or even avoids the need for a release modifying agent in order to obtain non-immediate release.

The preferred solid dosage form is a tablet. The average tablet weight is preferably about 15 mg to 1000 mg. It is contemplated that for certain uses, e.g., antacid tablets, or vaginal tablets, the tablet will be larger. Most oral tablets will fall will generally fall within the recited range. The amount of lubricant needed in the tablet is generally less than that needed for calcium phosphate itself and as mentioned above is preferably eliminated entirely by the presence of a sufficient amount of wax provided by the fatty acid wax modified calcium phosphate.

The modified calcium phosphate of the present invention can advantageously be used to make tablets by direct compression. Generally this process comprises dry mixing the modified calcium phosphate excipient with the active ingredient and optionally one or more excipients to form a tablet blend. This mixing can be done in one or more stages. The modified calcium phosphate of the present invention can be blended with additional excipients before, during or after blending with the active ingredient. In this regard, the modified calcium phosphate may be previously prepared and stored before use in the tablet blend or it may be formed as part of the tablet production process, i.e. as a "premix." The tablet blend preferably contains a proportion of the active agent that corresponds to an effective amount once tabletted. The tablet blend, i.e., at least a portion thereof, is compressed to form a tablet. The compression can be carried out using conventional tabletting equipment. For instance, tabletting can be performed in a production scale tabletting machine at normal compression pressures for that machine, e.g., about 1-100 kN.

Because the wax modified calcium phosphate excipient is generally hydrophobic, albeit different in nature to the calcium phosphate itself, it can produce a tablet matrix, if used in sufficient quality and quantity, that essentially maintains its structural integrity in aqueous environments. In this case, the tablet does not disintegrate in, e.g., the digestive tract fluid unless a specific disintegrant has been incorporated in the tablet composition. Instead, the tablet erodes, generally slowly. Accordingly, the hydrophobicity of the excipient can substantially reduce the access of water, including gastric or intestinal fluid, to the active substance. After tabletting the excipient with the active substance and with optional additional excipient(s), a tablet may be produced that exhibits slow or sustained release of the active from the composition in the environment of use. A possibility to make a controlled release dosage form by a simple compressing of the active substance with an excipient is a particular aspect and discovery of the present invention. Similarly, it is another aspect of the invention that a skilled person can make an in vitro correlation between the solubility of the active substance, the composition of the excipient and the release rate in order to predict how an active substance of certain solubility will be released in the body fluid.

The final rate of release of the active substance from the dosage form administered into the environment of use can be further modified by a variety of tools known in the art. For instance, the tablet composition may additionally comprise a disintegrant. The disintegrant separates the tablet matrix into a plurality of particles, thus increasing the overall surface of contact with the aqueous environment, and, accordingly, the rate of release of the active substance.

Similarly, the release rate may be positively modulated by a presence of non-hydrophobic release modulators, preferably hydrophilic polymers, the most preferred being hypromelose. Additionally, pore-forming excipients such as soluble excipients (e.g. lactose, mannitol, sorbitol, sucrose, aminoacids, etc.) may be present within the tablet composition, wherein the pore-forming agent increases the erosion rate of the matrix.

In certain embodiments of the invention, the formed tablet may be coated with a sufficient amount of a hydrophobic polymer to render the formulation capable of providing a desired release of the active agent such that a 12 or 24 hour formulation is obtained. Examples of suitable polymeric materials include ethylcellulose, hydroxypropylcellulose, hydroxypropylmethylcellulose, polyethylene oxides, sodium alginates, and the like.

In other embodiments of the present invention, the tablet coating may comprise an enteric coating material in addition to or instead of the hydrophobic polymer coating. Examples of suitable enteric polymers include cellulose acetate phthalate, hydroxypropylmethylcellulose phthalate, polyvinylacetate phthalate, methacrylic acid copolymer, shellac, hydroxypropylmethylcellulose succinate, cellulose acetate trimellitate, and mixtures of any of the foregoing. An example of a suitable commercially available enteric material is available under the trade name Eudragit™ L 100-55S.

In further embodiments, the dosage form may be coated with an esthetic coating in addition to or instead of the above-mentioned functional coatings. An example of a suitable material which may be used for such a coating is hydroxypropylmethylcellulose (e.g., Opadry®).

The coatings may be applied in any pharmaceutically acceptable manner known to those skilled in the art. For example, in one embodiment, the coating is applied via a fluidized bed or in a coating pan. The solvent for the polymer may be organic, aqueous, or a mixture of an organic and an aqueous solvent. The organic solvents may be, e.g., isopropyl alcohol, ethanol, and the like, with or without water. The coatings which may be optionally applied to the tablet of the invention may comprise from about 0.5% to about 30% by weight of the final tablet.

In additional embodiments of the present invention, a support platform is applied to the tablets manufactured in accordance with the present invention. Suitable support platforms are well known to those skilled in the art. The support platform may, for example, be designed to maintain its impermeability characteristics during the transfer of the therapeutically active medicament. The support platform may be applied to the tablets, e.g., via compression coating onto part of the tablet surface, by spray coating the polymeric materials comprising the support platform onto all or part of the tablet surface, or by immersing the tablets in a solution of the polymeric materials. Materials useful in the hydrophobic coatings and support platforms of the present invention include derivatives of acrylic acid (such as esters of acrylic acid, methacrylic acid, and copolymers thereof) celluloses and derivatives thereof (such as ethylcellulose), polyvinylalcohols, and the like.

In certain embodiments of the present invention, the tablet includes an additional dose of the medicament (pharmaceutically active agent) included in any or all of the coating layers on the outer surface of the tablet core. This may be desired when, for example, a loading dose of a therapeutically active agent is needed to provide therapeutically effective blood levels of the active agent when the formulation is first exposed to gastric fluid. The loading dose of medicament included in the coating layer may be, e.g., from about 10% to about 40% of the total amount of medicament included in the formulation.

Alternatively to tabletting by direct compression, the solid dosage form can be made by granulating optionally followed by tabletting. For example, the modified calcium phosphate excipient may be subjected to a wet, dry or melt granulation with the active agent to form an active granulate. A representative wet granulation includes loading the novel excipient particles into a suitable granulator, and granulating the particles together with the active ingredient, preferably using a granulating liquid. The granulating liquid is added to the mixture with stirring until the powdery mass has the consistency of damp snow and then wet screened through a desired mesh screen. The screened granulate is then dried, using standard drying apparatus such as a convection oven before undergoing a final screening. Additional dry screening of this material is possible. The material may be further ground prior to ultimate tablet formulation. Dry granulation and melt granulation processes leading to an active substance incorporated into granules, may also be performed by conventional procedures. The obtained active granulate is capable of undergoing tabletting, optionally with the addition of further excipients, wherein the tabletting conditions and tablet products are substantially similar as shown above or, alternatively, placed into a unit dosage form such as a capsule or a sachet, optionally with other excipients.

In certain embodiments, a portion of the total amount of the novel excipient is first granulated with the active ingredient, and thereafter the additional portion of the novel excipient is added to the granulate. In yet another embodiment, the active granulate is tabletted with an additional portion of the active agent, thus allowing for a tablet having double mode of release of the active substance with the matrix.

Preferred dosage form for industrial application of the excipient of the present invention is a tablet, particularly an orally administrable tablet. However, the formulations prepared in accordance with the present invention may be suitably shaped for other uses or locations, such as other body cavities, e.g., periodontal pockets, implants, suppositories etc. Alternatively, the novel excipient can be utilized in other applications wherein it is not compressed. For example, as shown above, the excipient can be admixed with an active agent by granulation and the granulate is then filled into capsules. The granulate can further be molded into shapes other than those typically associated with tablets. For example, the granulate together with active ingredient can be molded to "fit" into a particular area in an environment of use (e.g., an implant). All such uses would be contemplated by those skilled in the art.

Each of the patents mentioned above is incorporated herein by reference in its entirety. The invention will be further described with reference to the following non-limiting examples.

EXAMPLE 1

Four batches of the co-processed excipient of the invention were produced as follows:

| | Ratio w/w (%) | Weight (g) |
|---|---|---|
| Batch 1 | | |
| Dicalcium phosphate anhydrous (A-TAB ®) | 95 | 4750 |
| Glyceryl behenate (Compritol ® 888 ATO) | 5 | 250 |

| | Ratio w/w (%) | Weight (g) |
|---|---|---|
| Batch 2 | | |
| Dicalcium phosphate anhydrous (A-TAB ®) | 85 | 4250 |
| Glyceryl behenate (Compritol ® 888 ATO) | 15 | 750 |
| Batch 3 | | |
| Dicalcium phosphate anhydrous (A-TAB ®) | 70 | 3500 |
| Glyceryl behenate (Compritol ® 888 ATO) | 30 | 1500 |
| Batch 4 | | |
| Dicalcium phosphate anhydrous (A-TAB ®) | 50 | 2500 |
| Glyceryl behenate (Compritol ® 888 ATO) | 50 | 2500 |

Batches were prepared following the steps:

Mixing: Glyceryl behenate and dicalcium phosphate were mixed together in a high shear mixer Vagumator VMA10 (manufactured by L.B.Bohle Germany) at 200 rpm impellor speed ("IS") for 5 minutes.

Granulation: The jacket temperature of the high shear mixer was increased up to 45° C. and a microwave source of heating was connected (vacuum: 80 mbar, IS: 100 rpm). The product temperature increases up to about 80° C. Once this temperature is reached an intensification phase is carried out with a chopper mixer for 1 additional minute (IS 400 rpm) to reach maximum torque and temperature ranges from 76° to 94° C. The jacket temperature of the high shear mixer is decreased to 35° C. (IS: 50 rpm). The process was ended when the product cooled down to about 40° C. At this temperature granules were obtained.

Sieving: These granulates were sieved manually by a 710 microns screen (batches 2&3) or through a Bohle Turbo Sieve 100 equipped with a 1.1 mm screen (batches 1&4).

EXAMPLE 2

Dry Blend Mixtures—Four comparative batches were produced as a control as follows:

| | Ratio w/w (%) | Weight (g) |
|---|---|---|
| Batch 5 | | |
| Dicalcium phosphate anhydrous (A-TAB ®) | 95 | 1900 |
| Glyceryl behenate (Compritol ® 888 ATO) | 5 | 100 |
| Batch 6 | | |
| Dicalcium phosphate anhydrous (A-TAB ®) | 85 | 1700 |
| Glyceryl behenate (Compritol ® 888 ATO) | 15 | 300 |
| Batch 7 | | |
| Dicalcium phosphate anhydrous (A-TAB ®) | 70 | 1400 |
| Glyceryl behenate (Compritol ® 888 ATO) | 30 | 600 |
| Batch 8 | | |
| Dicalcium phosphate anhydrous (A-TAB ®) | 50 | 1000 |
| Glyceryl behenate (Compritol ® 888 ATO) | 50 | 1000 |

Mixing: Glyceryl behenate and dicalcium phosphate were mixed together in a Turbula mixer for 15 minutes. No treatment of the mixtures was undertaken.

EXAMPLE 3

A batch of the co-processed excipient of the invention was produced as follows:

| Batch 9 | Ratio w/w (%) | Weight (g) |
|---|---|---|
| Dicalcium phosphate dihydrate (DI-TAB ®) | 85 | 4250 |
| Glyceryl behenate (Compritol ® 888 ATO) | 15 | 750 |

Mixing: Glyceryl behenate and dicalcium phosphate were mixed together in a high shear mixer Vagumator VMA10 (manufactured by L.B.Bohle, Germany) at 200 rpm IS for 5 minutes.

Granulation: The jacket temperature of the high shear mixer was increased up to 45° C. and a microwave source of heating was connected (vacuum: 80 mbar, IS: 100 rpm). The product temperature increased up to 74.4° C. Once this temperature was reached an intensification phase is carried out with a chopper mixer for 1 additional minute (IS 400 rpm) to reach maximum torque and temperature arrives to 77.3° C. The jacket temperature of the high shear mixer is decreased to 30° C. (IS: 50 rpm). When the product reached 55° C. a second intensification phase is made with chopper mixer for 5 minutes (IS 200 rpm). After the intensification, granules are obtained. The process was ended when the product cooled down to about 35° C.

Sieving: This granulate was sieved (Bohle Turbo Sieve 100) through 1.1 mm screen.

EXAMPLE 4

Dry Blend Mixture—Comparative batch was produced as a control as follows:

| Batch 10 | Ratio w/w (%) | Weight (g) |
|---|---|---|
| Dicalcium phosphate dihydrate (DI-TAB ®) | 85 | 1700 |
| Glyceryl behenate (Compritol ® 888 ATO) | 15 | 300 |

Mixing: Glyceryl behenate and dicalcium phosphate were mixed together in a Turbula mixer for 15 minutes. No treatment of the mixture was undertaken.

EXAMPLE 5

A batch of the co-processed excipient of the invention was produced as follows:

| Batch 11 | Ratio w/w (%) | Weight (g) |
|---|---|---|
| Dicalcium phosphate anhydrous milled (DICAFOS ® PA) | 70 | 350 |
| Glyceryl behenate (Compritol ® 888 ATO) | 30 | 150 |

Mixing: Glyceryl behenate and dicalcium phosphate were mixed together in a high shear mixer Mi-Mi-Pro (manufactured by Pro-C-ept, Belgium) at 300 rpm IS for 3 minutes.

Granulation: The oven temperature of the high shear mixer is increased up to 50° C. and a microwave source of heating was connected (vacuum: 400 mbar, IS: 100 rpm). The product temperature increased up to 67.5° C. Once this temperature was reached, an intensification phase was carried out with a chopper mixer (1300 rpm) to reach maximum torque (from 30% to 48%) and temperature arrives to 70° C. The oven temperature of the high shear mixer is decreased to 25° C. After the intensification, "pellet like" granules were obtained (maximum size about 2 mm). The process was ended when the product cooled down to about 40° C.

Sieving: This granulate was sieved (Bohle Turbo Sieve 100) through 1.1 mm screen.

EXAMPLE 6

Dry Blend Mixture—Comparative batch was produced as a control as follows:

| Batch 12 | Ratio w/w (%) | Weight (g) |
|---|---|---|
| Dicalcium phosphate anhydrous milled (DICAFOS ® PA) | 70 | 350 |
| Glyceryl behenate (Compritol ® 888 ATO) | 30 | 150 |

Mixing: Glyceryl behenate and dicalcium phosphate were mixed together in a Turbula mixer for 15 minutes. Appearance is fine powder without homogeneous characteristics.

Sieving: Product was sieved manually by a 710 microns screen and mixed again in Turbula for 5 minutes.

EXAMPLE 7

A batch of the co-processed excipient of the invention was produced as follows:

| Batch 13 | Ratio w/w (%) | Weight (g) |
|---|---|---|
| Dicalcium phosphate anhydrous (A-TAB ®) | 70 | 350 |
| Glyceryl palmitostearate (Precirol ® 5 ATO) | 30 | 150 |

Mixing: Glyceryl palmitostearate and dicalcium phosphate were mixed together in a high shear mixer Mi-Mi-Pro (manufactured by Pro-C-ept, Belgium) at 400 rpm IS for 3 minutes.

Granulation: The oven temperature of the high shear mixer was increased up to 50° C. and a microwave source of heating was connected (vacuum: 400 mbar, IS: 100 rpm). The product temperature increased up to 53.4° C. Once this temperature was reached, an intensification phase is carried with chopper (1300 rpm) and without microwaves to reach maximum torque of 40%. The oven temperature of the high shear mixer is decreased to 30° C. After the intensification, granules were obtained. The process was ended when the product cooled down to about 30° C.

Sieving: This granulate was sieved manually by a 710 microns screen.

EXAMPLE 8

A batch of the co-processed excipient of the invention was produced as follows:

| Batch 14 | Ratio w/w (%) | Weight (g) |
|---|---|---|
| Dicalcium phosphate anhydrous (A-TAB ®) | 70 | 350 |
| Hydrogenated castor oil (Cutina ® HR) | 30 | 150 |

Mixing: Wax and dicalcium phosphate were mixed together in a high shear mixer Mi-Mi-Pro (manufactured by Pro-C-ept, Belgium) at 300-600 rpm IS for 3 minutes.

Granulation: The oven temperature of the high shear mixer was increased up to 50° C. and a microwave source of heating was connected (vacuum: 400 mbar, IS: 100 rpm). The product temperature increased up to 72.8° C. Once this temperature was reached, an intensification phase was carried out with a chopper mixer (1300 rpm) and without microwaves to reach maximum torque of 40%. The oven temperature of the high shear mixer was decreased to 20° C. After the intensification, pellet size granules were obtained (maximum size about 2 mm). The process was ended when the product cooled down to about 60° C., the product being completely solid. In this case, it was not even necessary to reach the melting point to produce a granulate.

Sieving: This granulate was sieved manually by a 710 microns screen.

EXAMPLE 9

Two batches of the co-processed excipient of the invention were produced as follows:

| Batches 15 & 16 | Ratio w/w (%) | Weight (g) |
| --- | --- | --- |
| Dicalcium phosphate anhydrous (A-TAB ®) | 70 | 350 |
| Glyceryl behenate (Compritol ® 888 ATO) | 15 | 75 |
| Glyceryl palmitostearate (Precirol ® 5 ATO) | 15 | 75 |

Mixing: Waxes and dicalcium phosphate were mixed together in a high shear mixer Mi-Mi-Pro (manufactured by Pro-C-ept, Belgium) at 300 rpm IS for 3 minutes.

Granulation: The oven temperature of the high shear mixer was increased up to 60° C. and a microwave source of heating was connected (vacuum: 400 mbar, IS: 100 rpm). The product temperature increased up to 54° C. in both batches before starting an intensification phase, carried out with a chopper mixer (1300 rpm) without/with microwaves to reach maximum torque of 30%.

First case (Batch 15) temperature ranges from 54.4° to 63.4° C.

Second case (Batch 16) temperature ranges from 54.1° to 72.6° C.

The oven temperature of the high shear mixer is decreased to 25° C. In the first case, only one wax was molten, in the second case both waxes were molten. Similar granules were obtained in both cases, indicating the robustness of the process.

Sieving: These granules were sieved manually by a 710 microns screen.

EXAMPLE 10

Two batches of the co-processed excipient of the invention were produced as follows:

| | Ratio w/w (%) | Weight (g) |
| --- | --- | --- |
| Batch 17 | | |
| Dicalcium phosphate anhydrous, dense powder (Dicafos ® A) | 35 | 35 |
| Glyceryl behenate (Compritol ® 888 ATO) | 65 | 65 |
| Batch 18 | | |
| Dicalcium phosphate anhydrous, coarse powder (Dicafos ® AN) | 60 | 60 |
| Glyceryl behenate (Compritol ® 888 ATO) | 40 | 40 |

Mixing: Waxes and dicalcium phosphate were mixed together in a high shear mixer Mi-Mi-Pro (manufactured by Pro-C-ept, Belgium) at 250 rpm IS for 3 minutes.

Granulation: The oven temperature of the high shear mixer was limited to room temperature (15° C. programmed) and microwaves were used as a unique source of heating (vacuum: 400 mbar, IS: 250 rpm). The product temperature increased up to 69-70° C. in both batches. No intensification phase was carried out, chopper mixer at minimum speed (130 rpm), to reach maximum torque of 13%.

In both cases a granulated mass was formed that can be processed further while warm obtaining granules, indicating robustness of the process.

Sieving: These granules were sieved manually, first through a 1.4 mm screen an after by a 710 microns screen.

EXAMPLE 11

Dry Blend Mixtures—Two comparative batches were produced as a control as follows:

| | Ratio w/w (%) | Weight (g) |
| --- | --- | --- |
| Batch 19 | | |
| Dicalcium phosphate anhydrous, dense powder (Dicafos ® A) | 35 | 35 |
| Glyceryl behenate (Compritol ® 888 ATO) | 65 | 65 |
| Batch 20 | | |
| Dicalcium phosphate anhydrous, coarse powder (Dicafos ® AN) | 60 | 60 |
| Glyceryl behenate (Compritol ® 888 ATO) | 40 | 40 |

Mixing: Glyceryl behenate and dicalcium phosphate were mixed together in a Turbula mixer for 15 minutes. No treatment of the mixture was undertaken.

EXAMPLE 12

Physical Analyses of the New Excipient

Density:

In order to show the density properties of the co-processed excipients, in comparison with the ordinary mixtures of the components, four values have been analyzed.

Bulk density: As described in Ph.Eur. About one hundred grams are poured in a graduated cylinder to measure the volume (bulk volume).

Tapped density: As described in Ph.Eur. About one hundred grams are compacted in a graduated cylinder using a volumenometer, tapping them at 1250 or 2500 strokes, and measuring the volume (bulk volume after tapping).

True density: As measured by gas pycnometry in a Quantachrome Helium Pycnometer. Result represents the skeletal volume of the solid material and closed pores without accounting the volume of the open pores and interparticle voids.

Porosity: Percent porosity has been calculated from measurements of bulk volume after tapping ($V_B$) and skeletal volume ($V_S$) by the relationship:

% Porosity=100*($V_B$-$V_S$)/$V_B$

| | DENSITY (g/ml) | | | |
|---|---|---|---|---|
| | BULK | TAPPED | TRUE | % POROSITY |
| A-TAB ® | 0.66-0.71 | 0.83-0.89 | 2.83-2.92 | 69.5-70.6 |
| Batch 1 | 0.86 | 1.02 | 2.82 | 63.8 |
| Batch 2 | 1.00 | 1.16 | 2.29 | 49.3 |
| Batch 3 | 0.91 | 1.03 | 1.87 | 44.9 |
| Batch 4 | 0.76 | 0.94 | 1.50 | 37.3 |
| Batch 5 | 0.71 | 0.85 | 2.77 | 69.3 |
| Batch 6 | 0.74 | 0.91 | 2.42 | 62.4 |
| Batch 7 | 0.72 | 0.88 | 1.95 | 54.9 |
| Batch 8 | 0.63 | 0.78 | 1.61 | 51.6 |

Bulk and tapped densities are higher for the co-processed excipient (batches 1-4) than for the comparative mixtures (batches 5-8). These mixtures have similar densities to the dicalcium phosphate used to manufacture them (A-TAB®), but with a tendency to segregate into its component materials. On the other hand, true density for the new co-processed excipients was lower for 15%, 30% and 50% of glyceryl behenate indicating reduction in total porosity. True density measurements have also detected the existence of closed pores in the new co-processed excipients.

Settlement, Free Flow and Angle of Repose:

In order to show these physical properties related to the free-flowing capacity of the co-processed excipients, in comparison with the ordinary mixtures of the components, three methods have been used.

Settlement: As described in Ph.Eur., is the difference between the volume of about one hundred grams of powder between 10 and 500 strokes, measured in a graduated cylinder.

Free Flow Rate: Rate to flow a product through a glass funnel of 12.5 mm diameter.

Angle of Repose: Measures the static angle, in degrees, that forms the cone of powder after flowing in the precedent test with the floor plane.

| | PHYSICAL PARAMETERS | | |
|---|---|---|---|
| | Settlement (ml) | Flow rate (g/s) | Angle of repose (°) |
| Batch 1 | 9.3 | 42.4 | 34.4 |
| Batch 2 | 5.3 | 47.5 | 34.1 |
| Batch 3 | 5.0 | 48.6 | no data |
| Batch 4 | 12.0 | 41.7 | 31.5 |
| Batch 5 | 13.0 | 34.4 | 34.3 |
| Batch 6 | 12.3 | 36.7 | 32.3 |
| Batch 7 | 22.0 | 0 | — |
| Batch 8 | 21.3 | 0 | — |
| Batch 9 | 10.7 | 60.6 | 36.5 |
| Batch 10 | 7.0 | 25.8 | 33.5 |

Settlement values are lower for the new co-processed excipients in comparison to the mixture, indicating fewer tendencies to segregate and better flowability. These enhanced properties are confirmed by the measured flow rates.

Flow Time:

In order to show the properties of these free-flowing co-processed excipients in comparison with the ordinary mixtures of the components two additional methods were assayed.

Test A: Time to flow 100 g of product, through stainless steel funnels of different apertures, recorded automatically and expressed in seconds.

Test B: Time to flow 100 g of product, through stainless steel funnels of different apertures (as reported in Ph. Eur.), recorded manually (3 runs average) in seconds.

| | FLOW TIME (seconds) | | | | | | |
|---|---|---|---|---|---|---|---|
| | Test A | | | | Test B | | |
| Hole ø (mm) | 5 | 10 | 15 | 20 | 10 | 15 | 25 |
| Batch 1 | 54.34 | 9.45 | 3.35 | 1.50 | 9.83 | 3.64 | 1.06 |
| Batch 2 | 34.36 | 5.84 | 2.12 | 0.97 | 5.91 | 2.08 | 0.63 |
| Batch 3 | 43.10 | 7.10 | 2.51 | 1.25 | 6.49 | 2.28 | 0.55 |
| Batch 4 | ∞ | ∞ | 5.96 | 1.80 | ∞ | ∞ | 1.84 |
| Batch 5 | 67.56 | 12.45 | 4.00 | 1.85 | 11.72 | 4.39 | 1.18 |
| Batch 6 | 74.07 | 13.28 | 4.73 | 2.19 | 14.77 | 5.48 | 1.65 |
| Batch 7 | ∞ | ∞ | ∞ | 6.45 | ∞ | 10.76 | 4.29 |
| Batch 8 | ∞ | ∞ | ∞ | 15.46 | ∞ | ∞ | 8.24 |
| Batch 9 | 35.21 | 5.59 | 2.06 | 0.94 | 5.65 | 1.95 | 0.65 |
| Batch 10 | 59.17 | 17.89 | 8.27 | 2.35 | 19.31 | 6.44 | 2.40 |

All the batches of co-processed excipient flow better, in all conditions, than equivalent compositions of physical mixtures (comparative batches). High glyceryl behenate quantities affect negatively the flow, but stay acceptable for co-processed excipients. Optimum flow is obtained with co-processed excipient with 5-30% glyceryl behenate (batches 1, 2, 3 and 9).

Surface analysis:

In order to show the surface properties of the co-processed excipients, in comparison with the ordinary mixtures of the components, and with dicalcium phosphate anhydrous (A-TAB®), specific surface area has been measured, using a Quantachrome Nova equipment, by the BET technique. Result represents the reactive surface area present in each sample.

pH: Since one of the differences after processing the excipient should be the surface pH, this value was measured in 20% (w/v) slurries in purified water using a Metrohm pH meter.

| | SURFACE ANALYSIS | | |
|---|---|---|---|
| | Single BET (g/m$^2$) | Multi BET (g/m$^2$) | pH |
| A-TAB ® | 16.01-16.58 | 16.43-16.90 | 5.12 |
| Batch 3 | 6.32 | 8.18 | 5.65 |
| Batch 7 | 9.98 | 10.29 | 5.16 |

Surface area is reduced significantly by the new co-processed excipient and the pH is more neutral. Both results may explain the stability results described in examples 15-20.

EXAMPLE 13

Placebo Tablets

In this example, placebo tablets were prepared in an instrumented Korsch tablet press EK0 having flat round punches of 100 mm² surface and with a chamber depth of 10 mm, to provide about 1 ml bulk volume filling. Two pressures were applied for each batch, low (2-4 kN) and high (10-16 kN). Details concerning the preparation of each product are set forth below.

|  | Weight (g) |
|---|---|
| Example 13a | |
| Co-processed Excipient (Batch 2, see example 1) | 198 |
| SiO₂ (AEROSIL ® 200) | 1 |
| Magnesium stearate | 1 |
| Example 13b | |
| Co-processed Excipient (Batch 2, see example 1) | 170 |
| Lactose (PHARMATOSE ® DCL11) | 28 |
| SiO₂ (AEROSIL ® 200) | 1 |
| Magnesium stearate | 1 |
| Example 13c | |
| Co-processed Excipient (Batch 2, see example 1) | 170 |
| Sorbitol (KARION ® INSTANT) | 28 |
| SiO₂ (AEROSIL ® 200) | 1 |
| Magnesium stearate | 1 |
| Example 13d | |
| Co-processed Excipient (Batch 3, see example 1) | 198 |
| SiO₂ (AEROSIL ® 200) | 1 |
| Magnesium stearate | 1 |
| Example 13e | |
| Co-processed Excipient (Batch 3, see example 1) | 170 |
| Lactose (PHARMATOSE ® DCL11) | 28 |
| SiO₂ (AEROSIL ® 200) | 1 |
| Magnesium stearate | 1 |
| Example 13f | |
| Co-processed Excipient (Batch 3, see example 1) | 170 |
| Sorbitol (KARION ® INSTANT) | 28 |
| SiO₂ (AEROSIL ® 200) | 1 |
| Magnesium stearate | 1 |

Manufacturing process: Aerosil and magnesium stearate were sieved, and mixed with the co-processed excipient in a Turbula mixer for 15 minutes. At least 200 tablets were produced for each example.

Disintegration test: Using HCl 0.01N (diluted acid) or HCl 0.15N (concentrated acid) as test fluids, disintegration tests were carried out by Ph. Eur. disintegration method. Tablets were maintained in the medium for two hours, then removed (if integrity was maintained) and dried overnight (40° C., vacuum<100 mbar). Afterwards, weight and hardness were measured and compared with the theoretical original.

| | Pressure (kN) | Weight (mg) | Hardness (N) | HCl 0.01 N | HCl 0.15 N |
|---|---|---|---|---|---|
| Example 13a | 3.5 | 1015.42 | 37.94 | Resist | Resist |
| | 10.9 | 1016.96 | 121.30 | Resist | Resist |
| Example 13b | 3.5 | 935.44 | 34.44 | Disintegrate | Disintegrate |
| | 11.1 | 942.34 | 117.00 | Resist | Resist |
| Example 13c | 3.1 | 640.56 | 35.45 | Disintegrate | Disintegrate |
| | 15.2 | 648.52 | 194.61 | Resist | Resist |
| Example 13d | 2.5 | 1009.08 | 67.89 | Resist | Resist |
| | 13.7 | 1006.18 | 161.41 | Resist | Resist |
| Example 13e | 2.8 | 940.30 | 62.44 | Resist | Resist |
| | 13.5 | 938.40 | 160.29 | Resist | Resist |
| Example 13f | 2.6 | 916.86 | 66.45 | Resist | Resist |
| | 11.6 | 921.86 | 173.62 | Resist | Resist |

As can be observed, tablets made with a hydrophilic excipient, 15% of wax, and low pressure, disintegrated while the rest of the tablets made with the co-processed excipient resist (did not disintegrate in) the acidic media. This was surprising as dicalcium phosphate dissolves freely in acid conditions and is the major component of all formulations tested.

All the tablets resist perfectly in purified water, even for 24 hours.

| | | % Weight maintained | | % Hardness maintained | |
|---|---|---|---|---|---|
| | Pressure (kN) | HCl 0.01 N | HCl 0.15 N | HCl 0.01 N | HCl 0.15 N |
| Example 13a | 3.5 | 84.6 | 56.8 | 47.2 | 31.4 |
| | 10.9 | 93.7 | 75.5 | 63.7 | 70.1 |
| Example 13b | 3.5 | — | — | — | — |
| | 11.1 | 83.9 | 53.0 | 36.9 | 40.0 |
| Example 13c | 3.1 | — | — | — | — |
| | 15.2 | 86.3 | 51.5 | 59.9 | 49.1 |
| Example 13d | 2.5 | 96.9 | 86.6 | 71.3 | 78.5 |
| | 13.7 | 97.4 | 90.3 | 76.4 | 78.0 |
| Example 13e | 2.8 | 89.3 | 79.6 | 82.2 | 88.2 |
| | 13.5 | 93.4 | 84.7 | 100.9 | 108.6 |
| Example 13f | 2.6 | 89.7 | 77.4 | 89.9 | 86.2 |
| | 11.6 | 92.4 | 82.1 | 70.6 | 85.6 |

EXAMPLE 14

In this example, placebo tablets were prepared in an instrumented Korsch tablet press EK0. Two different tablet sizes and shapes were used:
- Flat round punches of 100 mm² surface and with a chamber depth of 10 mm, to provide about 1 ml bulk volume filling. Two pressures were applied for each batch, low (6+/−1 kN) and high (12+/−1 kN).
- Concave round punches of 7 mm diameter and an aim weight of 140 mg were used for compressibility study, at four different pressures.

Details concerning the preparation of each product are set forth below.

|  | Weight (g) |
|---|---|
| Example 14a | |
| Co-processed Excipient (Batch 1, see example 1) | 495.0 |
| SiO₂ (AEROSIL ® 200) | 2.5 |
| Magnesium stearate | 2.5 |

|  | Weight (g) |
|---|---|
| Example 14b | |
| Co-processed Excipient (Batch 2, see example 1) | 495.0 |
| SiO₂ (AEROSIL ® 200) | 2.5 |
| Magnesium stearate | 2.5 |
| Example 14c | |
| Co-processed Excipient (Batch 3, see example 1) | 495.0 |
| SiO₂ (AEROSIL ® 200) | 2.5 |
| Magnesium stearate | 2.5 |
| Example 14d | |
| Co-processed Excipient (Batch 4, see example 1) | 495.0 |
| SiO₂ (AEROSIL ® 200) | 2.5 |
| Magnesium stearate | 2.5 |
| Example 14e comparative | |
| Comparative mixture (Batch 5, see example 2) | 495.0 |
| SiO₂ (AEROSIL ® 200) | 2.5 |
| Magnesium stearate | 2.5 |
| Example 14f comparative | |
| Comparative mixture (Batch 8, see example 2) | 495.0 |
| SiO₂ (AEROSIL ® 200) | 2.5 |
| Magnesium stearate | 2.5 |

Manufacturing process: Aerosil and magnesium stearate were sieved, and mixed with the co-processed excipient or comparative mixture in a Turbula mixer for 15 minutes. At least 200 tablets were produced for each example.

Disintegration test: Using HCl 0.01 N or purified water as test fluids, disintegration tests were carried out by Ph. Eur. disintegration method. Tablets were maintained in the medium for two hours, then removed (if integrity was maintained) and dried (40° C., vacuum <100 mbar, 24 h). Afterwards, weight and hardness were measured and compared with the theoretical original.

|  | Pressure (kN) | Weight (mg) | Hardness (N) | HCl 0.01 N | Water |
|---|---|---|---|---|---|
| Example 14a | 6.6 | 877.36 | 36.44 | Resist* | Resist |
|  | 11.5 | 881.34 | 71.65 | Resist* | Resist |
| Example 14b | 6.3 | 987.80 | 78.50 | Resist | |
|  | 12.1 | 993.62 | 138.37 | Resist | |
| Example 14c | 5.1 | 1072.93 | 129.14 | Resist | |
|  | 12.4 | 1074.80 | 153.13 | Resist | |
| Example 14d | 6.4 | 727.25 | 68.40 | Resist | |
|  | 11.4 | 731.84 | 76.48 | Resist | |
| Example 14e | 5.5 | 763.57 | 31.17 | Resist* | Resist |
|  | 13.1 | 769.46 | 80.40 | Resist* | Resist |
| Example 14f | 5.3 | 694.24 | 55.63 | Resist | |
|  | 13.1 | 692.76 | 73.42 | Resist | |

*Tablets are observed as very porous systems

As can be observed, all tablets resisted, but the ones having only 5% of wax (examples 14a and 14e) were clearly affected by the acid medium, and these tests were repeated with purified water. Resistance, measured as percentage of weight or hardness maintained after 2 hours, was also similar for all batches, and should provide enough integrity to resist transit through the gastrointestinal tract.

|  | Pressure (kN) | % Weight maintained | | % Hardness maintained | |
|---|---|---|---|---|---|
|  |  | HCl 0.01 N | Water | HCl 0.01 N | Water |
| Example 14a | 6.6 | 85.7 | 97.8 | 60.6 | 69.2 |
|  | 11.5 | 89.2 | 98.3 | 62.4 | 63.8 |
| Example 14b | 6.3 | 93.0 |  | 70.0 |  |
|  | 12.1 | 93.2 |  | 81.2 |  |
| Example 14c | 5.1 | 97.8 |  | 94.0 |  |
|  | 12.4 | 98.3 |  | 101.9 |  |
| Example 14d | 6.4 | 96.8 |  | 107.5 |  |
|  | 11.4 | 97.5 |  | 103.7 |  |
| Example 14e | 5.5 | 84.6 | 98.1 | 106.8 | 97.7 |
|  | 13.1 | 86.7 | 97.0 | 83.4 | 81.2 |
| Example 14f | 5.3 | 97.2 |  | 112.1 |  |
|  | 13.1 | 97.3 |  | 96.9 |  |

Tablets made with co-processed excipient or simple mixtures behave similarly in disintegration, but compression properties are better for the co-processed excipient.

EXAMPLES 15

Bisoprolol Hemifumarate Tablets

In these examples, the tablet products were prepared in an instrumented Korsch tablet press EK0 having capsule-shaped concave punches of 16 mm length, 8 mm width and weighing 920 or 1000 mg. The details concerning the preparation of each product are set forth below.

|  | Weight/tablet (mg) |
|---|---|
| Example 15 | |
| Bisoprolol hemifumarate | 10 |
| Co-processed Excipient (Batch 1, see example 1) | 900 |
| Magnesium stearate | 10 |
| Example 16 | |
| Bisoprolol hemifumarate | 10 |
| Co-processed Excipient (Batch 3, see example 1) | 900 |
| Magnesium stearate | 10 |
| Example 17 | |
| Bisoprolol hemifumarate | 10 |
| Co-processed Excipient (Batch 3, see example 1) | 900 |
| Pregelatinized starch (STARCH 1500 ®) | 50 |
| Crospovidone (POLYPLADONE ® XL) | 20 |
| Magnesium stearate | 20 |
| Example 18 comparative | |
| Bisoprolol hemifumarate | 10 |
| Dicalcium phosphate anhydrous (A-TAB ®) | 900 |
| Magnesium stearate | 10 |
| Example 19 comparative | |
| Bisoprolol hemifumarate | 10 |
| Dicalcium phosphate anhydrous (A-TAB ®) | 855 |
| Glyceryl behenate (Compritol ® 888 ATO) | 45 |
| Magnesium stearate | 10 |
| Example 20 comparative | |
| Bisoprolol hemifumarate | 10 |
| Dicalcium phosphate anhydrous (A-TAB ®) | 900 |
| Pregelatinized starch (STARCH 1500 ®) | 50 |
| Crospovidone (POLYPLADONE ® XL) | 20 |
| Magnesium stearate | 20 |

Manufacturing process: Bisoprolol hemifumarate was mixed with the rest of the excipients, except the lubricant, for 15 minutes in a Turbula mixer. Magnesium stearate was sieved, added and mixed additionally for 5 minutes. At least 500 tablets were produced for each example.

Stickiness: It was not possible to compress Comparative Example 18 because of severe stickiness and adherence to the punches. Comparative Example 19 (5% of wax acts as a lubricant) and Example 20 (additional excipients help tabletting) had some adherence, but could be processed. All the Examples with the co-processed excipient show no adherence and were compressed without trouble.

Stability samples: Tablets were conditioned at 25° C./60% RH or 40° C./75% RH during three weeks before analyzing the impurities.

Analytical method: Degradation of bisoprolol occurs primarily by cleavage of the benzyl ether followed by oxidation to produce an aldehyde (bisobenzaldehyde). Degradation of bisoprolol fumarate in tablet dosage forms is accelerated when granular dicalcium phosphate anhydrous is used (Wendy A. Dulin, Drug Development and Industrial Pharmacy, 21(4), 393-409, 1995). Determination of the bisobenzaldehyde was performed by measuring the peak area (relative retention time 0.40-0.45) in the samples, using a High Pressure Liquid Chromatography (HPLC, Agilent 1100 series) equipped with a Diode Array Detector. Tablet samples were prepared with a solvent solution of phosphate buffer/acetonitrile ratio 85:15 (V/V), extraction in ultrasonic bath during 15 min and filtering to obtain a theoretical concentration of 0.7 mg/ml. For bisoprolol, the chromatographic conditions included a Symmetry column from (C18, 100×4.6 mm, $d_p$=3.5 μm) and a Sentry Guard Symmetry column (C18, $d_p$=5 μm), both from Waters, a gradient mobile phase (perchlorate/acetonitrile ratio of 93:7 (V/V) & perchlorate/acetonitrile ratio of 20:80 (V/V)) at a flow rate of 1.0 ml/min, UV detection (272 nm), injection volume of 25 μl (push loop) and a run time of 36 min.

Results: The impurity levels of bisobenzaldehyde was found as shown in the following table.

| Sample | Results of impurity "bisobenzaldehyde" after 3 weeks (area, mAU · s) | |
|---|---|---|
| | 25° C./60% RH | 40° C./75% RH |
| Example 15 | 9 | 1838 |
| Example 16 | 15 | 125 |
| Example 17 | 4 | 38 |
| Example 18 comparative | 347 | not processed |
| Example 19 comparative | 225 | 3616 |
| Example 20 comparative | 78 | 1017 |

The process of forming this impurity is reduced with the co-processed excipient of the invention.

EXAMPLES 21-23

Tamsulosin Hydrochloride Tablets

In these examples, active tablet products were prepared in an instrumented Korsch tablet press EK0 having concave round punches of 6 mm diameter and weighing 80 mg. The details of the preparation of each product are set forth below.

| | Weight/tablet (mg) |
|---|---|
| Example 21 | |
| Tamsulosin hydrochloride | 0.4 |
| Lactose anhydrous (PHARMATOSE ® DCL21) | 25.6 |
| Hypromellose (METHOCEL ® K100M) | 28.0 |
| Co-processed Excipient (Batch 1, see example 1) | 25.6 |
| Magnesium stearate | 0.4 |
| Example 22 | |
| Tamsulosin hydrochloride | 0.4 |
| Lactose anhydrous (PHARMATOSE ® DCL21) | 25.6 |
| Hypromellose (METHOCEL ® K100M) | 28.0 |
| Co-processed Excipient (Batch 3, see example 1) | 25.6 |
| Magnesium stearate | 0.4 |
| Example 23 comparative | |
| Tamsulosin hydrochloride | 0.4 |
| Lactose anhydrous (PHARMATOSE ® DCL21) | 25.6 |
| Hypromellose (METHOCEL ® K100M) | 28.0 |
| Dicalcium phosphate anhydrous (A-TAB ®) | 25.6 |
| Magnesium stearate | 0.4 |

Manufacturing process: Micronized tamsulosin hydrochloride was homogenized in a ratio 1:10 with lactose anhydrous (Turbula, 15 min), and afterwards mixed with the rest of the excipients, except the lubricant, for 15 minutes in a Turbula mixer. Magnesium stearate was sieved, added and mixed additionally for 5 minutes. At least 200 tablets were produced for each example.

Stability samples: Tablets were conditioned at 60° C. during one month and compared with time zero results.

Analytical method: Determination of the impurities present in the tablets related with tamsulosin degradation is performed by measuring the peak areas between retention times 5.1 min. and 5.4 min. in the samples, using an High Pressure Liquid Chromatography (HPLC, Agilent 1100 series) equipped with a Diode Array Detector. Tablet samples are prepared with a solvent (methanol) extraction in ultrasonic bath during 5 min, centrifuging at 3000 rpm 5 min. and filtering to obtain a theoretical concentration of 0.4 mg/ml. For tamsulosin, the chromatographic conditions included a Symmetry column from (C18, 100×4.6 mm, $d_p$=3.5 μm) and a Sentry Guard Symmetry column (C18, $d_p$=5 μm), both from Waters, a gradient mobile phase (phosphate buffer/acetonitrile ratio of 95:5 (V/V) & phosphate buffer/acetonitrile ratio of 20:80 (V/V)) at a flow rate of 1.0 ml/min, UV detection (279 nm), injection volume of 10 μl and a run time of 20 min.

Results: The impurities following the processing in the examples 21-23 are shown in next table. The process of degradation of tamsulosin is clearly reduced with the co-processed excipient of this invention.

| | Results of impurities at 60° C. (%) | |
|---|---|---|
| | Time | |
| | start (t = 0) | 1 month |
| Example 21 | not detectable | 0.04 |
| Example 22 | not detectable | not detectable |
| Example 23 comparative | not detectable | 0.54 |

EXAMPLES 24-33

Venlafaxine Tablets

In these examples, active tablet products were prepared in an instrumented Korsch tablet press EK0 having concave round punches of 5 mm diameter and weighing 80 mg. The details concerning the preparation of each product are set forth below.

| | Weight/tablet (mg) |
|---|---|
| Example 24 | |
| Venlafaxine | 37.5 |
| Co-processed Excipient (Batch 2, see example 1) | 41.7 |
| Magnesium stearate | 0.8 |
| Example 25 | |
| Venlafaxine | 37.5 |
| Co-processed Excipient (Batch 2, see example 1) | 37.7 |
| Lactose (PHARMATOSE ® DCL11) | 4.0 |
| Magnesium stearate | 0.8 |
| Example 26 | |
| Venlafaxine | 37.5 |
| Co-processed Excipient (Batch 2, see example 1) | 33.7 |
| Lactose (PHARMATOSE ® DCL11) | 8.0 |
| Magnesium stearate | 0.8 |
| Example 27 | |
| Venlafaxine | 37.5 |
| Co-processed Excipient (Batch 3, see example 1) | 41.7 |
| Magnesium stearate | 0.8 |
| Example 28 | |
| Venlafaxine | 37.5 |
| Co-processed Excipient (Batch 3, see example 1) | 37.7 |
| Lactose (PHARMATOSE ® DCL11) | 4.0 |
| Magnesium stearate | 0.8 |
| Example 29 | |
| Venlafaxine | 37.5 |
| Co-processed Excipient (Batch 3, see example 1) | 33.7 |
| Lactose anhydrous (PHARMATOSE ® DCL21) | 8.0 |
| Magnesium stearate | 0.8 |
| Example 30 | |
| Venlafaxine | 37.5 |
| Co-processed Excipient (Batch 4, see example 1) | 40.9 |
| SiO₂ (AEROSIL ® 200) | 0.8 |
| Magnesium stearate | 0.8 |

Manufacturing process: Venlafaxine was mixed with the co-processed excipient and lactose or Aerosil (if included) for 15 minutes in a Turbula mixer. Magnesium stearate was sieved, added and mixed additionally for 5 minutes. At least 500 tablets were produced for each example.

| | Weight/tablet (mg) |
|---|---|
| Example 31 comparative | |
| Venlafaxine | 37.5 |
| Dicalcium phosphate anhydrous (A-TAB ®) | 35.4 |
| Glyceryl behenate (Compritol ® 888 ATO) | 6.3 |
| Magnesium stearate | 0.8 |
| Example 32 comparative | |
| Venlafaxine | 37.5 |
| Dicalcium phosphate anhydrous (A-TAB ®) | 29.2 |

-continued

| | Weight/tablet (mg) |
|---|---|
| Glyceryl behenate (Compritol ® 888 ATO) | 12.5 |
| Magnesium stearate | 0.8 |
| Example 33 comparative | |
| Venlafaxine | 37.5 |
| Dicalcium phosphate anhydrous (A-TAB ®) | 20.45 |
| Glyceryl behenate (Compritol ® 888 ATO) | 20.45 |
| SiO₂ (AEROSIL ® 200) | 0.8 |
| Magnesium stearate | 0.8 |

Manufacturing process: Direct mixtures of dicalcium phosphate and glyceryl behenate were prepared and mixed with Venlafaxine and Aerosil (if included) for 15 minutes in a Turbula mixer. Magnesium stearate was sieved, added and mixed additionally for 5 minutes. At least 500 tablets were produced for each example.

Dissolution profiles: The dissolution tests were carried out by USP method 1 (basket apparatus) using 900 ml Simulated Intestinal Fluid (SIF, pH 6.8) at 37° C., speed rotation was set at 100 rpm (Vankel system). Sampling was carried out at predetermined intervals and the drug was assayed by UV method (Cary spectrophotometer) and is expressed as percentage of the declared amount.

| | Results of in vitro dissolution test (%) (SIF pH 6.8, Baskets, 100 rpm) | | | | |
|---|---|---|---|---|---|
| | Time (h) | | | | |
| | 0 | 2 | 4 | 8 | 12 |
| Example 24 | 0 | 31.3 | 41.9 | 58.4 | 69.1 |
| Example 25 | 0 | 32.7 | 45.3 | 62.7 | 75.8 |
| Example 26 | 0 | 33.0 | 47.0 | 67.6 | 82.3 |
| Example 27 | 0 | 28.9 | 38.4 | 51.2 | 60.5 |
| Example 28 | 0 | 31.2 | 42.4 | 57.2 | 67.5 |
| Example 29 | 0 | 33.8 | 45.8 | 61.9 | 73.5 |
| Example 30 | 0 | 27.1 | 35.8 | 47.4 | 55.9 |
| Example 31 | 0 | 30.5 | 41.8 | 58.8 | 69.5 |
| Example 32 | 0 | 24.3 | 34.3 | 47.6 | 57.0 |
| Example 33 | 0 | 19.9 | 29.1 | 41.8 | 51.1 |

EXAMPLES 34-38

Paroxetine Mesylate Tablets

In these examples, active tablet products were prepared in an instrumented Korsch tablet press EK0 having concave round punches of 5 mm diameter and weighing 80 or 90 mg. The details concerning the preparation of each product are set forth below.

| | Weight/tablet (mg) |
|---|---|
| Example 34 | |
| Paroxetine mesylate | 16.14* |
| Co-processed Excipient (Batch 2, see example 1) | 62.26 |
| SiO₂ (AEROSIL ® 200) | 0.8 |
| Magnesium stearate | 0.8 |
| Example 35 | |
| Paroxetine mesylate | 16.14* |
| Co-processed Excipient (Batch 2, see example 1) | 54.26 |

-continued

| | Weight/tablet (mg) |
|---|---|
| Sorbitol (KARION ® INSTANT) | 8.0 |
| SiO$_2$ (AEROSIL ® 200) | 0.8 |
| Magnesium stearate | 0.8 |
| Example 36 | |
| Paroxetine mesylate | 12.5 |
| Co-processed Excipient (Batch 3, see example 1) | 75.7 |
| SiO$_2$ (AEROSIL ® 200) | 0.9 |
| Magnesium stearate | 0.9 |
| Example 37 | |
| Paroxetine mesylate | 16.14* |
| Co-processed Excipient (Batch 3, see example 1) | 54.26 |
| Lactose anhydrous (PHARMATOSE ® DCL21) | 8.0 |
| SiO$_2$ (AEROSIL ® 200) | 0.8 |
| Magnesium stearate | 0.8 |
| Example 38 | |
| Paroxetine mesylate | 12.5 |
| Co-processed Excipient (Batch 4, see example 1) | 75.7 |
| SiO$_2$ (AEROSIL ® 200) | 0.9 |
| Magnesium stearate | 0.9 |

*equivalent to 12.5 mg paroxetine

Manufacturing process: Paroxetine mesylate was mixed with the co-processed excipient, lactose or sorbitol (if included) and Aerosil for 15 minutes in a Turbula mixer. Magnesium stearate was sieved, added and mixed additionally for 5 minutes. At least 500 tablets were produced for each example.

EXAMPLE 39

In this example, active tablet product was scaled-up to an instrumented Korsch rotary tablet press XL100 having concave round punches of 6 mm diameter and weighing 80 mg.

| Example 39 | |
|---|---|
| Paroxetine mesylate | 605.3 g |
| Co-processed Excipient (Batch 3, see example 1) | 1945 g |
| Sorbitol (KARION ® INSTANT) | 420 g |
| SiO$_2$ (AEROSIL ® 200) | 15 g |
| Magnesium stearate | 15 g |

Manufacturing process: Paroxetine mesylate was mixed with the co-processed excipient, sorbitol and Aerosil for 15 minutes in a Bohle LM40 mixer. Magnesium stearate was sieved, added and mixed additionally for 5 minutes.

Dissolution profiles: The dissolution tests were carried out by USP method 1 (basket apparatus) using 900 ml Simulated Intestinal Fluid (SIF, pH 6.8) at 37° C., speed rotation was set at 100 rpm (Vankel system). Sampling was carried out at predetermined intervals and the drug was assayed by UV method (Cary spectrophotometer) and is expressed as percentage of the declared amount.

| Results of in vitro dissolution test (%) (SIF pH 6.8, Baskets, 100 rpm) | | | | | | | |
|---|---|---|---|---|---|---|---|
| | Time (h) | | | | | | |
| | 0 | 1 | 2 | 3 | 4 | 5 | 6 |
| Example 34 | 0 | 31.1 | 47.2 | 58.6 | 68.0 | 73.0 | 77.4 |
| Example 35 | 0 | 33.7 | 51.3 | 62.8 | 70.4 | 75.8 | 79.5 |
| Example 36 | 0 | 28.2 | 38.6 | 45.3 | 50.2 | 54.4 | 57.7 |
| Example 37 | 0 | 34.6 | 50.1 | 59.3 | 65.8 | 70.9 | 75.1 |
| Example 38 | 0 | 24.7 | 31.8 | 36.2 | 39.5 | 42.3 | 44.5 |
| Example 39 | 0 | 43.6 | 63.3 | 74.7 | 82.0 | 87.1 | 90.7 |

EXAMPLE 40

Paroxetine Mesylate Coated Tablets

Core (Uncoated Tablets)

Formulation

| | Weight (mg) |
|---|---|
| Paroxetine mesylate | 16.14 mg |
| Anhydrous dicalcium phosphate (A-tab ®) | 52.92 mg |
| Glyceryl behenate (Compritol ® ATO 888) | 9.34 mg |
| Magnesium stearate | 0.80 mg |
| Silicon dioxide (Aerosil ® 200) | 0.80 mg |
| Total weight | 80.00 mg |

Process of Making the Modified Calcium Phosphate

Mixing: Glyceryl behenate and Anhydrous dicalcium phosphate were mixed together in a high shear mixer Vagumator VMA 10 (Manufactured by L.B.Bohle, Germany) using impeller at 250 rpm for 5 minutes.

Granulation: The jacket temperature of the high shear mixer was increased up to 45° C. and microwaves source of heating was connected (vacuum: 80 mbar, impeller speed: 100 rpm). The product temperature increased up to about 80° C. Once this temperature was reached an intensification phase was carried out with chopper mixer for 1 additional minute (impeller speed: 400 rpm) to reach maximum torque and temperature ranges from 76° C. to 94° C. The jacket temperature of the high shear mixer was decreased to 35° C. (impeller speed: 50 rpm). The process ended when the product cooled down to about 40° C. At this temperature, granules were obtained.

Sieving: The granules were sieved manually through a 710 microns screen.

Tabletting Process

Paroxetine mesylate and silicon dioxide were added to the granules and this mixture was sieved through 710 microns screen and mixed in a Turbula mixer for 15 minutes. Magnesium stearate was added to the mixture and mixed in a Turbula mixer for 5 minutes. Compression was carried out in an instrumented Korsh tablet eccentric press EK0 obtaining biconvex round 5 mm diameter, 80 mg weight tablets.

Coating

Formulation

|  | Coating suspension |
| --- | --- |
| Eudragit RL 30 D | 980.0 g |
| Triethyl citrate | 58.8 g |
| Magnesium stearate | 44.1 g |
| Simethicone emulsion 30% | 1.5 g |
| Purified water | 987.9 g |
| Total coating suspension | 2072.3 g |

Process

Coating: The previous tablets (uncoated tablets) were coated in a BLC 5/10 coating equipment (manufactured by L.B.Bohle, Germany).

The coating parameters were:
 Drum speed: 15-20 rpm
 Spray solution rate: 8-12 g/min
 Inlet air flow: 120 Nm"/h
 Inlet air temperature: 40-45° C.
 Tablet temperature: 30-35° C.

Dissolution Profiles

The dissolution test was carried out by USP method (basket apparatus) using 900 ml Simulated Intestinal Fluid (SIF, pH 6.8) at 37° C., speed rotation was set at 100 rpm (Vankel system). Sampling was carried out at predetermined intervals and the drug was assayed by UV method (Cary spectrometer) and is expressed as percentage of the declared amount.

| Results in vitro dissolution test (%) (SIF pH 6.8, Baskets 100 rpm) | | | | | | | |
| --- | --- | --- | --- | --- | --- | --- | --- |
| | Time (hours) | | | | | | |
| % coating | 0 | 1 | 2 | 4 | 8 | 12 | 24 |
| 0% (uncoated tablets) | 0 | 36.1 | 53.0 | 75.1 | 90.5 | 95.7 | 103.0 |
| 4% | 0 | 2.7 | 7.6 | 16.4 | 30.9 | 44.0 | 71.8 |

Observations:
 The uncoated tablets remained intact after 24 hours dissolution profile. These tablets dissolve by tortuosity through the porosity created in the cores during the dissolution of the drug.
 Coated tablets did not show a coating layer around them after 24 hours dissolution profile.

The invention having been described it will be obvious that the same may be varied in many ways and all such modifications are contemplated as being within the scope of the invention as defined by the following claims.

We claim:

1. An excipient composition comprising calcium phosphate modified with a fatty acid wax, wherein a weight ratio of said calcium phosphate to said wax is within the range of 50:50 to 95:5.

2. The excipient composition according to claim 1, wherein said weight ratio of calcium phosphate:wax is within the range of 60:40 to 85:15.

3. The excipient composition according to claim 1, wherein said wax is selected from the group consisting of palmitic acid, behenic acid, stearic acid, glyceryl behenate, glyceryl palmitostearate, hydrogenated castor oil, and mixtures thereof.

4. The excipient composition according to claim 3, wherein said wax is glyceryl behenate.

5. The excipient composition according to claim 4, wherein said weight ratio of calcium phosphate to glyceryl behenate is within the range of 60:40 to 85:15.

6. The excipient composition according to claim 1, wherein said calcium phosphate is an anhydrous dibasic calcium phosphate.

7. The excipient composition according to claim 1, wherein said excipient composition is in a particulate form.

8. The excipient composition according to claim 7, wherein said particles have an average size within the range of 50 to 500 microns.

9. The excipient composition according to claim 8, wherein the average size of said particles is within the range of 125 to 250 microns.

10. The excipient composition according to claim 8, wherein said particulate form is substantially monodisperse such that at least 50% of said particles have a size within 20 microns of the average particle size.

11. The excipient composition according to claim 8, wherein said composition has an angle of repose within the range of 20° to 40°.

12. A solid dosage form comprising an effective amount of an active agent and the excipient composition according to claim 1.

13. The solid dosage form according to claim 12, wherein said active agent is a pharmaceutically active agent.

14. The solid dosage form according to claim 13, wherein said form is a tablet.

15. The solid dosage form according to claim 14, wherein said excipient composition is contained in said tablet in an amount of at least 40% by weight.

16. The solid dosage form according to claim 15, wherein said amount of excipient composition is at least 70% by weight.

17. The solid dosage form according to claim 14, wherein said excipient composition and said pharmaceutically active agent taken together total an amount that is at least 85% of said tablet by weight.

18. A particle, consisting essentially of a calcium phosphate particle having a fatty acid wax at least partially coated thereon, impregnated therein, or both; said particle having a size within the range of 125 to 250 microns and said calcium phosphate and said wax present in a weight ratio of calcium phosphate:wax that is within the range of 50:50 to 95:5.

* * * * *